United States Patent [19]

Kodama et al.

[11] Patent Number: 5,756,862
[45] Date of Patent: May 26, 1998

[54] PRODUCTION OF OPTICALLY ACTIVE 2-HALO-1-(SUBSTITUTED PHENYL)ETHANOL AND SUBSTITUTED STYRENE OXIDE

[75] Inventors: Hiroki Kodama; Takuya Motokawa, both of Sakai; Hiroshi Yamaguchi, Kawachinagano; Masanori Yoshida, Hashimoto, all of Japan

[73] Assignee: Nihon Nohyaku Co., Ltd., Tokyo, Japan

[21] Appl. No.: 699,457

[22] Filed: Aug. 19, 1996

[30] Foreign Application Priority Data

Aug. 26, 1995  [JP]  Japan ................................. 7-240730

[51] Int. Cl.$^6$ ............................................. C07C 29/74
[52] U.S. Cl. ........................... 568/810; 568/812; 549/518
[58] Field of Search .............................. 568/810, 812; 549/518

[56] References Cited

U.S. PATENT DOCUMENTS

| | | | |
|---|---|---|---|
| 3,879,476 | 4/1975 | Deli et al. | 568/812 |
| 4,857,468 | 8/1989 | Kutsuki et al. | 435/280 |
| 4,996,158 | 2/1991 | Oda et al. | 435/280 |
| 5,266,485 | 11/1993 | Sawa et al. | 435/280 |

FOREIGN PATENT DOCUMENTS

A 60-218387   11/1985   Japan.
A-4-218384    8/1992    Japan.

OTHER PUBLICATIONS

Hartgerink, J.W. "Photochemically Initiated Reactions of Substituted 1,3–dioxolanes and 1,3–oxathiolanes in CFC13" Tetrahedron, vol. 27, pp. 4323–4334, 1971.
Hartgerink, J.W., et al., "Photochemically initiated reactions of substituted 1,3–dioxolanes and 1,3–oxathiolanes in CFCl$_3$," *Tetrahedron*, vol. 27, pp. 4323–4334 (1971).
Organic Reactions, vol. II, Chapter 9, A.W. Ingersoll "The Resolution of Alcohols", [Acid Phthalate and Succinates—p. 385+], pp. 376–414, 1994.
J. Org. Chem. American Chemical Society, 1992, 57. "The Osmium–Catalyzed Asymmetric Dihydroxylation: A New Ligand Class and a Process Improvement", K.B. Sharpless et al., pp. 2768–2771.
Kagaku Sousetsu, No. 6, "Separation of optical isomers", p. 8, Nippon Kagakukai, 1989.
Modern Synthetic Methods, vol. 5, pp. 115–198 (1989).

*Primary Examiner*—C. Warren Ivy
*Assistant Examiner*—Lyman H. Smith
*Attorney, Agent, or Firm*—Oliff & Berridge, PLC

[57] ABSTRACT

A process for producing optically active 2-halo-1-(substituted phenyl)ethanol of a formula (Ia) or optically active styrene oxide of a formula (Ib). The process comprises the steps of reacting a compound of a formula (II) with phthalic anhydride to give a compound of a formula (III), performing optical resolution on the resulting compound using an optically active organic amine as a resolving agent, and finally performing hydrolysis or alcoholysis on the optically resolved compound (Ia) or (Ib). The scheme of the above process is:

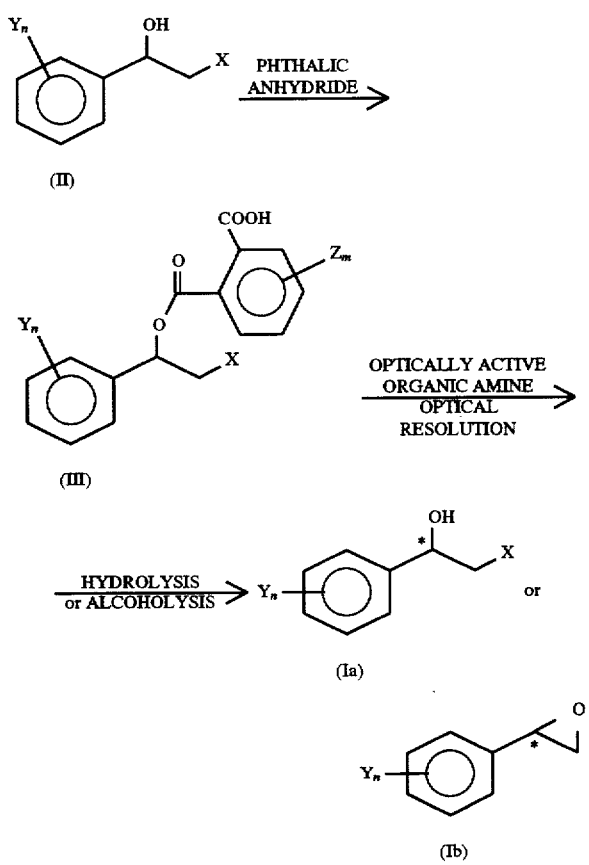

wherein X represents a halogen atom, Y represents a hydrogen atom, a halogen atom, a $C_1$–$C_6$ alkyl group, a $C_1$–$C_6$ alkoxy group, a $C_1$–$C_6$ haloalkyl group or a $C_1$–$C_6$ haloalkoxy group, Z represents a hydrogen atom, a halogen atom or a $C_1$–$C_6$ alkyl group, n is 0 or an integer of 1 to 3 and m is 0 or an integer of 1 to 2. The resulting optically active compounds are useful as an intermediate for medicines.

3 Claims, No Drawings

PRODUCTION OF OPTICALLY ACTIVE 2-HALO-1-(SUBSTITUTED PHENYL)ETHANOL AND SUBSTITUTED STYRENE OXIDE

BACKGROUND OF THE INVENTION

1. Field of the Invention

The present invention relates to a process for producing optically active 2-halo-1-(substituted phenyl)ethanol and substituted styrene oxide and for heightening optical purity of 2-halo-1-(substituted phenyl)ethanol.

The optically active 2-halo-1-(substituted phenyl)ethanol produced according to the process of the present invention is useful as an optically active intermediate for medicines and agricultural chemicals. For example, it may be used for the production of optically active ketene S,S-acetals as disclosed in Japanese Patent Application Laid-open No. Sho 60-218387 (218387/1985).

2. Description of the Prior Art

Optically active styrene oxide may be produced with the aid of microorganisms as disclosed in Japanese Patent Application Laid-open No. Hei 4-218384 (218384/1992); it may also be produced from styrene by conversion into asymmetric diol as reported by K. B. Sharpless et al. [J.O.C.(1992), 57, 2768] However, these processes for asymmetric synthesis are not necessarily satisfactory from the standpoint of operating efficiency, yields, optical purity, and production cost.

There has long been a known process for converting a racemic alcohol into a phthalate ester and optically resolving it using an adequate resolving agent. [A. W. Ingersoll (1994), Org. React., vol. 2, 376] However, nothing is mentioned therein about the compound such as 2-halo-1-(substituted phenyl)ethanol, which has substituent groups in the benzene ring and alkyl chain. There is a literature which mentions that there exists no principle that can be applied, in resolution of diastereomers, to the selection of a resolving agent and the resolving procedure suitable for a certain compound and the selection and the resolving methods should be made on the trial-and-error basis. ("Kagaku Sousetsu" No. 6, Separation of optical isomers, p. 8, "Nippon Kagakukai", 1989) Under these circumstances, there has been a demand for a new process for producing 2-halo-1-(substituted phenyl)ethanol of a formula (Ia) and optically active substituted styrene oxide of a formula (Ib) by the diastereomer resolving method which is satisfactory from the standpoint of yields and optical purity.

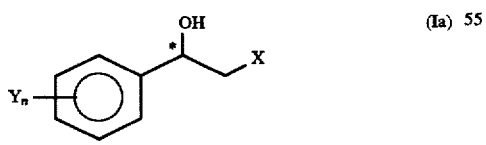

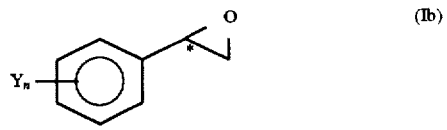

wherein X represents a halogen atom, Y is same or different and represents a hydrogen atom, a halogen atom, a $C_1$–$C_6$ alkyl group, a $C_1$–$C_6$ alkoxy group, a $C_1$–$C_6$ haloalkyl group or a $C_1$–$C_6$ haloalkoxy group, n is 0 or an integer of 1 to 3, and represents an asymmetric carbon atom.

In the above definition of substituent groups in the formula (Ia) and (Ib), the halogen atom includes chlorine, bromine, fluorine, and iodine atoms, and the $C_1$–$C_6$ alkyl group includes straight chain or branched alkyl groups having 1-6 carbon atoms, such as methyl, ethyl, n-propyl, i-propyl, n-butyl, i-butyl, s-butyl, t-butyl, n-pentyl, and n-hexyl groups. The $C_1$–$C_6$ alkoxy group includes straight chain or branched alkoxy groups such as a methoxy group, an ethoxy group, an n-propoxy group, an i-propoxy group, an n-butoxy group, an n-pentyloxy group and an n-hexyloxy group. The $C_1$–$C_6$ haloalkyl group includes straight chain or branched haloalkyl groups such as trifluoromethyl group. The $C_1$–$C_6$ haloalkoxy group includes straight chain and branched haloalkoxy groups such as difluoromethoxy group.

SUMMARY OF THE INVENTION

The present inventors carried out a series of intensive researches on the optical resolution of phthalate ester of 2-halo-1-(substituted phenyl)ethanol. As the result, they found processes for efficiently producing 2-halo-1-(substituted phenyl)ethanol of the formula (Ia) and optically active substituted styrene oxide of the formula (Ib) by optical resolution with the aid of an optically active organic amine as a resolving agent and subsequent hydrolysis or alcoholysis and a process for heightening an optical purity of 2-halo-1-(substituted phenyl)ethanol. These findings led to the present invention.

Thus, the present invention is to provide a process for producing an optically active compound useful as an intermediate for medicines and the other chemicals.

DESCRIPTION OF THE PREFERRED EMBODIMENTS

The productions of 2-halo-1-(substituted phenyl)ethanol of the formula (Ia) and optically active substituted styrene oxide of the formula (Ib) according to the present invention may be exemplified by the scheme illustrated below.

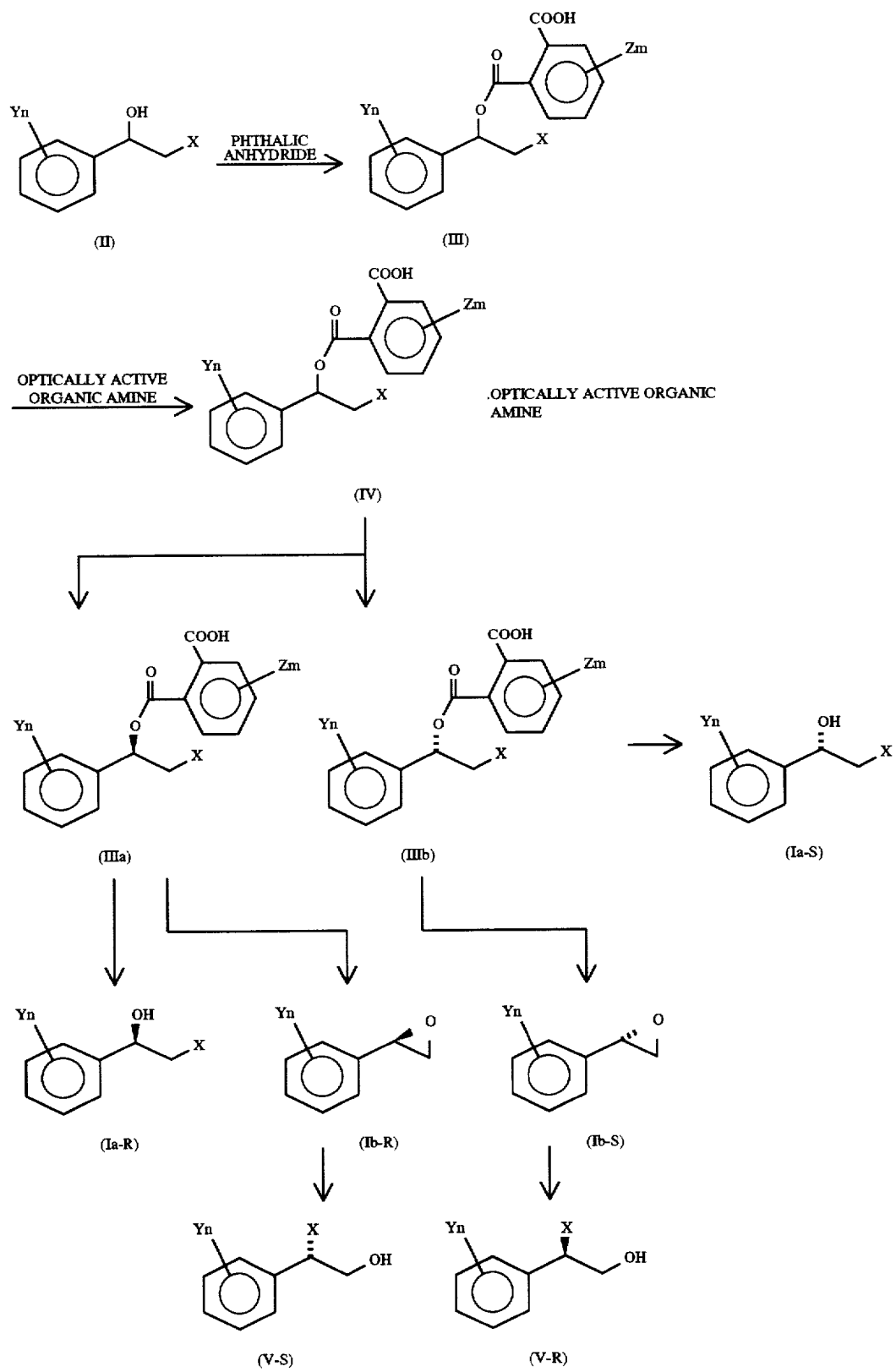
wherein X represents a halogen atom, Y is same or different and represents a hydrogen atom, a halogen atom, a $C_1$–$C_6$ alkyl group, a $C_1$–$C_6$ alkoxy group, a $C_1$–$C_6$ haloalkyl group or a $C_1$–$C_6$ haloalkoxy group, and n is 0 or an integer of 1 to 3, and Z represents a hydrogen atom, a halogen atom or a $C_1$–$C_6$ alkyl group and m is 0 or an integer of 1 to 2.

The optically active organic amine includes, for example, α-methylbenzylamine, α-ethylbenzylamine, 1-(p-tolyl) ethyl-amine, quinidine, cinchonidine, brucine, 2-amino-1,2-diphenylethanol, 1-phenyl-2-(4-tolyl)ethylamine and 1-naphthylamine.

(1) The racemic 2-halo-1-(substituted phenyl)ethanol of the formula (II) is converted, by any known method, into its phthalate of the formula (III). [A. W. Ingersoll (1994), Org. React., vol. 2, 376] In other words, the phthalate of 2-halo-1-(substituted phenyl)ethanol of the formula (III) can be produced by heating phthalic anhydride and 2-halo-1-(substituted phenyl)ethanol of the formula (II) in an inert solvent such as benzene, toluene, tetrahydrofuran (THF), acetone, and pyridine. The reaction may be accelerated by using a base such as triethylamine and 4-dimethylaminopyridine in a catalytic amount or in an excess amount as required.

(2) The racemic phthalate of 2-halo-1-(substituted phenyl) ethanol of the formula (III) undergoes optical resolution. In this step, the phthalate of the formula (III) is dissolved or suspended in a suitable inert solvent and reacted with a (+) or (−) optically active organic amine to give a diastereomer salt of the formula (IV), which subsequently undergoes resolution. In this case, it is possible to permit either one of the salt to separate out selectively. It is also possible to perform fractional crystallization in a suitable inert solvent. Resolution may be accomplished with the aid of a resolving agent such as optically active amines such as a α-methylbenzylamine in an amount of 0.5 to 2.0 mol., preferably 0.5 to 1.1 mol., relative to the phthalate of the formula (III). The mixture of chiral amine such as a α-methylbenzylamine and achiral amine such as triethylamine can also be used as optically resolution agent. In this case, the amount of chiral amine is enough when it is 0.5 to 1.0 mol., preferably 0.5 to 0.8 mol., relative to the phthalate of the formula (III).

Examples of the inert solvent include water, methanol, ethanol, isopropanol, acetone, methyl ethyl ketone, ethyl acetate, diethyl ether, diisopropyl ether, methylene chloride, chloroform, carbon tetrachloride, benzene, toluene, xylene, n-hexane, and cyclohexane. They may be used alone or in combination with one another. Preferred examples include ethanol, isopropanol, acetone, and methyl ethyl ketone, and their mixtures such as water/ethanol, water/isopropanol, n-hexane/ethanol, n-hexane/isopropanol, n-hexane/acetone, and n-hexane/ethyl acetate. The amount of the solvent is usually 1 to 150 times (by weight) as much as the solute, depending on the solubility of the diastereomer salt.

(3) The optically resolved diastereomer salt is converted in the usual way into a free phthalate of optically active 2-halo-1-(substituted phenyl)ethanol of the formula (IIIa) or (IIIb). This reaction may be accomplished in an adequate inert solvent by the action of an inorganic acid such as hydrochloric acid, sulfuric acid and nitric acid or organic acid such as acetic acid, toluenesulfonic acid and trifluoro-acetic acid in an equimolar amount.

(4) The optically active styrene oxide of the formula (Ib) can be produced from the phthalate of optically active 2-halo-1-(substituted phenyl)ethanol of the formulas (IIIa) and (IIIb) by alkali hydrolysis in a suitable inert solvent. Examples of the inert solvent include water, methanol, ethanol, isopropanol, acetone, methyl ethyl ketone, ethyl acetate, diethyl ether, diisopropyl ether, methylene chloride, chloroform, carbon tetrachloride, benzene, toluene, xylene, n-hexane, and cyclohexane. They may be used alone or in combination with one another. Preferred examples include toluene, alcohol/water mixture and acetone/water mixture. The amount of the solvent is usually 2 to 100 times (by weight) as much as the solute, depending on solubility. The base for alkali hydrolysis includes inorganic bases such as sodium hydroxide, potassium hydroxide, calcium hydroxide, potassium carbonate, sodium carbonate, and sodium hydrogen carbonate and organic bases such as triethylamine. Preferred examples include potassium carbonate, sodium hydrogen carbonate and sodium hydroxide. The amount of the base is usually 1 to 5 times (in mole) the amount of the phthalate of the optically active 2-halo-1-(substituted phenyl)ethanol of the formula (IIIa) or (IIIb). The reaction temperature ranges from 0° C. to 50° C., preferably 10 ° C. to 35 ° C.

(5) The optically active styrene oxide of the formula (Ib) undergoes ring opening by hydrogen halide in an adequate inert solvent so as to give the optically active 2-halo-2-(substituted phenyl)ethanol of the formulas (V-R) and (V-S). Examples of the inert solvent include diethyl ether, diisopropyl ether, tetrahydrofuran (THF), dioxane, ethanol, isopropanol, acetone, ethyl acetate, benzene, toluene, chloroform, and carbon tetrachloride. The amount of the solvent is usually 2 to 150 times (by weight) as much as the solute, depending on solubility. Examples of the hydrogen halide include hydrogen chloride, hydrogen bromide, and hydrogen iodide in anhydrous state. The amount of the hydrogen halide ranges from an equal amount to an excess amount.

(6) The optically active 2-halo-1-(substituted phenyl)-ethanol of the formula (Ia) can be produced from the phthalate of the optically active 2-halo-1-(substituted phenyl)ethanol of the formula (IIIa) or (IIIb) by acid hydrolysis in an adequate inert solvent. Examples of the inert solvent include water, methanol, ethanol, isopropanol, dimethoxyethane, acetone, methyl ethyl ketone, ethyl acetate, diethyl ether, diisopropyl ether, dioxane, methylene chloride, chloroform, carbon tetrachloride, benzene, toluene, xylene, n-hexane, and cyclohexane. They may be used alone or in combination with one another. Preferred examples include mixed solvents of water/alcohol, water/dioxane, and water/dimethoxyethane. The amount of the solvent is usually 2 to 150 times (by weight) as much as the solute, depending on solubility. The acid for hydrolysis may be an inorganic or organic acid, such as hydrochloric acid, sulfuric acid, acetic acid, toluenesulfonic acid, and trifluoroacetic acid. The amount of the acid is 1 to 50 times (in mole) the amount of the substrate. The reaction temperature ranges from 0° C. to 150° C., preferably 50° C. to 100° C.

(7) The optically active 2-halo-1-(substituted phenyl)-ethanol of the formula (Ia) is also produced by alcoholysis of the optically active phthalic acid derivative (III) in the presence of acids or bases.

The acids used in the present invention include, for example, inorganic acids such as hydrochloric acid and sulfuric acid or organic acids such as acetic acid and toluenesulfonic acid. The bases include, for example, inorganic bases such as sodium hydroxide, potassium hydroxide and potassium carbonate and organic bases such as triethylamine. The amount of these acids and bases may be optionally selected within the range between a catalytic amount and an excess amount.

Alcohols used for the alcoholysis include, for example, methanol, ethanol, n-propanol, i-propanol and n-butanol. The amount of the solvent may be optionally selected from the range that a solute is dissolved. The amount of the solvent is usually 2 to 150 times (by weight) as much as the solute, depending on the solubility.

The reaction temperature may be selected the range between 1° and 150° C., preferably, within the range between 50° and 100° C. The reaction time is depend on the reaction amount, reaction temperature, etc., but it may be within the range between 1 to 24 hours, preferably, from 2 to 6 hours.

alone or in combination with one another. Examples of the acid include inorganic acids such as hydrochloric acid, sulfuric acid and nitric acid and organic acids such as acetic acid, toluenesulfonic acid and trifluoromethanesulfonic acid.

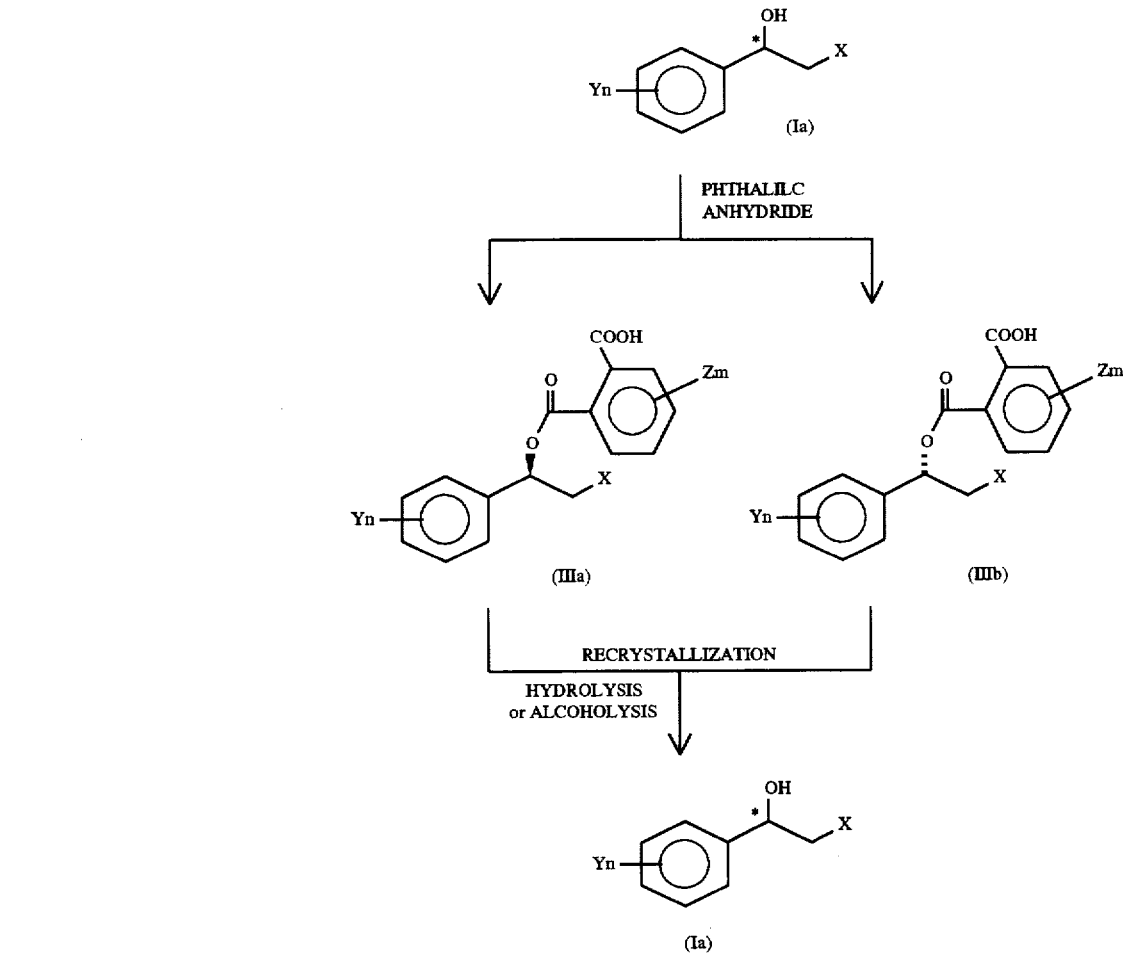

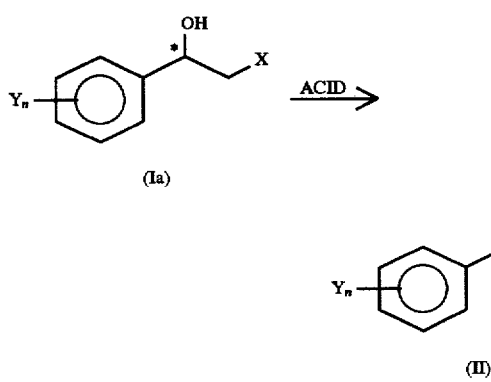

wherein X, Y, n and * have the same meanings as defined above. The optically active 2-halo-1-(substituted phenyl) ethanol of the formula (Ia) can be racemized in an adequate inert solvent in the presence of an adequate acid catalyst. Examples of the inert solvent include water, methanol, ethanol, isopropanol, dioxane, tetrahydrofuran (THF), dimethoxyethane, and ethyl cellosolve. They may be used wherein X, Y, Z, m, n and * have the same meanings as defined above. In order to heighten the optical purity of the optically active 2-halo-1-(substituted phenyl)ethanol of the formula (Ia), the compound (Ia) was reacted with a phthalic anhydride or a substituted phthalic anhydride to give optically active phthalic acid derivatives of the formula (IIIa). The compounds (IIIa) are purified by a recrystallization process to heighten their optical purity and thereafter, hydrolyzed or alcoholyzed to obtain the optically active 2-halo-1-(substituted phenyl)ethanol of the formula (Ia).

The reaction of the optically active 2-halo-1-(substituted phenyl)ethanol of the formula (Ia) to produce the optically active phthalic acid derivatives of the formula (IIIa) is conducted with a phthalic acid derivative such as an phthalic anhydride, etc. under heating in the presence of an inert solvent such as benzene, toluene, tetrahydrofuran (THF), acetonitrile and pyridine. In this reaction, the bases such as triethylamine and dimethylamine may be used within the range between a catalytic amount and an excess amount.

The solvents used in the recrystallization of the optically active phthalic acid derivatives of the formula (IIIa) are, for example, water, alcohols such as methanol or ethanol, ketones such as acetone and methyl ethyl ketone, THF, acetonitrile, ethyl acetate, n-hexane, n-heptane, dichloromethane, chloroform, carbon tetrachloride, benzene, toluene and xylene. They may be used alone or in combination with one another. Preferable solvents are in combinations of ethyl acetate, n-hexane, n-heptane, dichloromethane, chloroform and carbon tetrachloride.

The optically active phthalic acid derivatives of the formulas (IIIa) and (IIIb) the optical purity of which is heightened by this process are hydrolyzed or alcoholyzed in the presence of acids or bases to produce 2-halo-1-(substituted phenyl)ethanol of the formula (Ia) having high optical purity.

The following formula (III') shows the formula (IIIa) and the formula (IIIb).

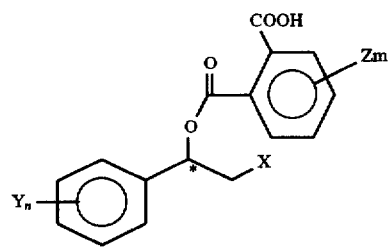

(10) The optical purity was determined by HPLC equipped with an optically active column, such as "Chiralcel OD" (trade name) and "Chiralcel OJ" (trade name) manufactured by Daicel Chemical Industries, Ltd. Measurements are based on the ratio of the area at a wavelength for maximum absorption or at a wavelength of 254 nm (UV). The absolute configuration of the compound was determined from the retention time in HPLC equipped with an optically active column (such as "Chiralcel OD" and "Chiralcel OJ") for the reference substance which is optically active 2-halo-1-(substituted phenyl)ethanol or compounds derived therefrom, the former being prepared from a substituted phenacyl halide according to the known method [Modern Synthetic Method, 5, 115, (1989)].

The process of the present invention yields those compounds of the formulas (Ia-S) and (V-S), which are useful as an intermediate for ketenedithioacetal derivative (A) useful as medicines and agricultural chemicals to be produced according to the scheme shown below.

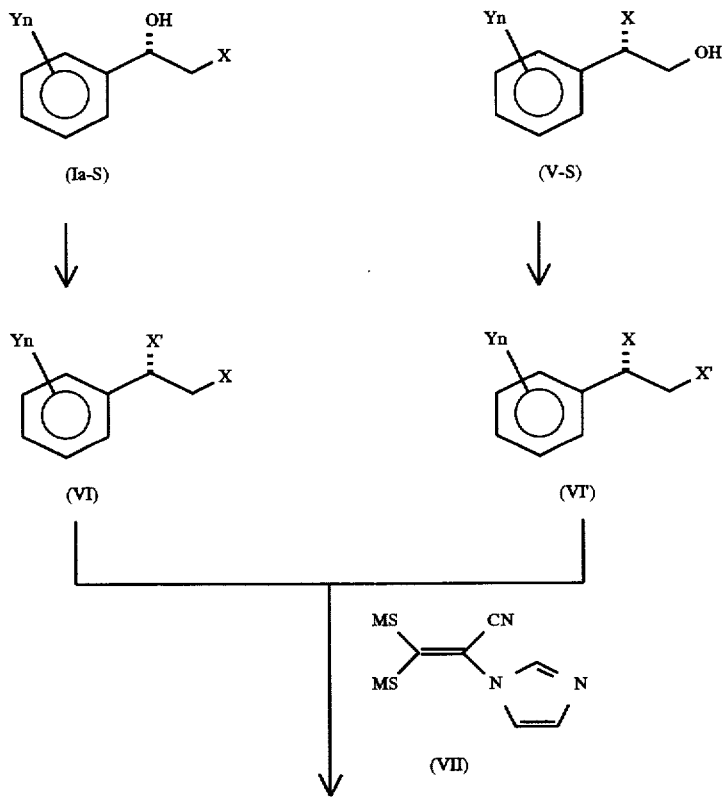

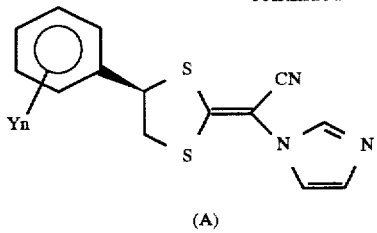

(A)

wherein X, Y and n have the same meaning as defined above, and X' represents a halogen atom, methanesulfonyloxy group or toluenesulfonyloxy group, and M represents an alkali metal atom.

Following is typical examples of the present invention. However, the present invention is not to be limited thereby.

EXAMPLE 1

Production of racemic (2-chloro-1-(2,4-dichlorophenyl)ethyl) hydrogenphthalate

In 10 ml of pyridine were dissolved 1.0 g of racemic 2-chloro-1-(2,4-dichlorophenyl)ethanol and 0.66 g of phthalic anhydride. The solution was refluxed for 3 hours in the presence of 0.1 g of dimethylaminopyridine. After the reaction was completed, the reaction mixture was cooled to room temperature and the solvent was distilled off under reduced pressure. The residues were dissolved in ethyl acetate, and the solution was washed with 1N-hydrochloric acid, washed with water, and dried over anhydrous magnesium sulfate. Finally, the solvent was distilled off under reduced pressure to obtain 1.2 g of the intended product. (yield: 72%, m.p. 156° to 157° C.)

The following compounds are produced by the similar processes.

(2-chloro-1-(2,4-dichlorophenyl)ethyl)4- or 5-Chlorohydrogenphthalate (yield: 75.6%, m.p. 144° to 147° C.

(2-chloro-1-(2,4-dichlorophenyl)ethyl)4,5-dichlorohydrogenphthalate (yield: 78.0%, m.p. 188° to 190° C.

(2-chloro-1-(2,4-dichlorophenyl)ethyl)4- or 5-methyl-hydrogenphthalate (yield: 16.3%, m.p. 127° to 130° C.

(2-chloro-1-(4-methoxyphenyl)ethyl)hydrogenphthalate (yield: 64%, m.p. 112° to 115° C.) (2-chloro-1-(4-methylphenyl)ethyl)hydrogenphthalate (yield: 59%, m.p. 128° to 131° C.) (2-chloro-1-)3-chlorophenyl)ethyl) hydrogenphthalate (yield: 59%, m.p. 125° to 128° C.)

EXAMPLE 2

Production of racemic (2-chloro-1-(2,4-dichlorophenyl)ethyl) hydrogenphthalate

In 150 ml of toluene were dissolved 20.0 g of racemic 2-chloro-1-(2,4-dichlorophenyl)ethanol and 13.1 g of phthalic anhydride. The solution was refluxed for 3 hours in the presence of 20 ml of triethylamine. After the reaction was completed, the reaction mixture was cooled to room temperature and the solvent was distilled off under reduced pressure. The residues were dissolved in ethyl acetate, and the solution was washed with 1N-hydrochloric acid, washed with water, and dried over anhydrous magnesium sulfate. Finally, the solvent was distilled off under reduced pressure to obtain 29.5 g of the intended product. (yield: 89%, m.p. 156° to 157° C.)

EXAMPLE 3

Production of (+)-α-methylbenzylamine salt of racemic (2-chloro-1-(2,4-dichlorophenyl)ethyl) hydrogenphthalate In 100 ml of ethyl acetate were completely dissolved 8.0 g of racemic (2-chloro-1-(2,4-dichlorophenyl)ethyl)-hydrogen phthalate and 2.6 g of (+)-α-methylbenzylamine to prepare an uniform solution. The solution was concentrated under reduced pressure to give crystals. The crystals were subsequently dried over reduced pressure to obtain 10.6 g of the intended product. (yield: 100%, m.p. 113° to 115° C.)

EXAMPLE 4

Diasteromer separation and double decomposition of (+)-α-methylbenzylamine salt of racemic (2-chloro-1-(2,4-dichlorophenyl)ethyl) hydrogenphthalate In 72 ml of a mixed solvent of ethanol/n-hexane (1:7) dissolved with heating 1.0 g of (+)-α-methylbenzylamine salt of racemic (2-chloro-1-(2,4-dichlorophenyl)ethyl) hydrogenphthalate. The solution was cooled at −5° C. for 10 hours for crystallization. Collecting the crystals by filtration gave 0.3 g of (+)-α-methylbenzylamine salt of (S)-(2-chloro-1-(2,4-dichlorophenyl)ethyl) hydrogenphthalate. The obtained optical isomer (0.3 g) was dissolved in 10 ml of acetone with heating, and 25 ml of 1N-hydrochloric acid was added to the solution. The solvent was distilled off under reduced pressure. Crystals that had separated out were filtered off, rinsed, and dried to obtain 0.22 g of (2-chloro-1-(2,4-dichlorophenyl)ethyl) hydrogenphthalate (94% ee, S-form). (yield: 28.2%, m.p. 144° to 145° C.)

The obtained (2-chloro-1-(2,4-dichlorophenyl)ethyl) hydrogenphthalate was esterified with trimethylsilyldiazomethane, and the resulting methyl ester was analyzed by HPLC (solvent: n-hexane/isopropanol=80/1, UV=254) equipped with an optically active column ("Chiralcel OD"). The optical purity was calculated from the percentage of the area of the chromatogram.

Similar processes were conducted in accordance with the Example 4 by using another optically active amines instead of R-(+)-phenethyl amine used in the Example 4. The result is shown in Table 1.

TABLE 1

| Optically active amine | Yield (%) | Optical purity (%) | Solvents used for recrystallization |
|---|---|---|---|
| Brucine | 26.2 | 60.7 | acetone |
| (1R,2S)-(-)-2-amino-1,2-diphenylethanol | 13.0 | 83.7 | ethanol |
| (S)-1-phenyl-2-(p-tolyl)-ethylamine1 | 14.0 | 85.0 | ethanol/n − hexane = ½ |
| (S)-(-)-(naphtyl)-ethylamine | 30.0 | 94.7 | ethanol/n − hexane = ½ |

EXAMPLE 5-1

Optical resolution of racemic [(2-chloro-1-(2,4-dichlorophenyl)ethyl] hydrogenphthalate by (+)-α-methylbenzylamine 329.1 g of racemic [2-chloro-1-(2,4-dichlorophenyl) ethyl] hydrogenphthalate (0.881 mol) obtained in the Example 2 were added to 7 Q of a solution of ethanol/n-hexane (=1:5) and heated to 48° to 50° C. After 106.7 g of (+)-α-methylbenzylamine (0.881 mol) were added to the solution at the same temperature, the resulting solution was ice-cooled to be crystallized. After 3-hour crystallization, crystals were collected by filtration and washed with 300 ml of an ice-cooled solution of ethanol/n-hexane (=1:5) to obtain 168.4 g of (+)-α-methylbenzylamine salt of (S)-[2-chloro-1-(2,4-dichlorophenyl)ethyl] hydrogenphthalate of the formula (IIIb). (optical purity: 96.7%, yield: 38.6%)

By the similar process, (2-chloro-1-(2,4-dichlorophenyl)ethyl)4- or 5-chlorohydrogenphthalate (5-2), (2-chloro-1-(2, 4-dichlorophenyl)ethyl) 4,5-dichlorohydrogenphthalate (5-3), (2-chloro-1-(2,4-dichlorophenyl)ethyl) 4- or 5-methyl-hydrogenphthalate (5-4), (2-chloro-1-(4-methylphenyl)ethyl) hydrogenphthalate (5-5), (2-chloro-1-(4-methoxyphenyl)ethyl) hydrogenphthalate (5-6) and (2-chloro-1-(3-chloromethyl)ethyl) hydrogenphthalate (5-7) were optically resolved.

The result is shown in Table 2.

TABLE 2

| Example No. | Yield (%) | Optical purity (%) |
|---|---|---|
| 5-2 | 22.8 | 64 |
| 5-3 | 24.9 | 70 |
| 5-4 | 26.7 | 33 |
| 5-5 | 28.0 | 23 |
| 5-6 | 20.0 | 42 |
| 5-7 | 18.0 | 70 |

EXAMPLE 6

Production of (R)-1-(2,4-dichlorophenyl)-1,2-ethylene oxide

In a mixed solvent composed of 5 ml of ethanol and 1 ml of water were dissolved 0.37 g of (S)-(2-chloro-1-(2,4-dichlorophenyl)ethyl) hydrogenphthalate (94% ee) and 0.22 g of 95% potassium hydroxide. The solution was stirred at room temperature for 1.5 hours. After the reaction was completed, the solvent was distilled off under reduced pressure. The residues were dissolved in 10 ml of water and the intended product was extracted with diethyl ether. The organic layer was washed with water and dried over anhydrous magnesium sulfate. The solvent was distilled off under reduced pressure to obtain 0.18 g of the intended product (93% ee). (yield: 96%).

The optical purity was calculated from the percentage of the area of the chromatogram of HPLC (solvent: n-hexane, UV=225) equipped with an optically active column ("Chiralcell OJ").

EXAMPLE 7-1

Production of (S)-1-(2,4-dichlorophenyl)-2-chloro-1-ethanol

In 20 ml of dioxane was dissolved 0.28 g of (S)-(2-chloro-1-(2,4-dichlorophenyl)ethyl) hydrogenphthalate (94% ee) obtained in Example 4. To the solution was added 10 ml of concentrated hydrochloric acid, and the solution was refluxed for 9 hours. After the reaction was completed, the reaction mixture was cooled to room temperature and the solvent was distilled off under reduced pressure. The residues were dissolved in 50 ml of diethyl ether and the solution was washed with water and dried with anhydrous magnesium sulfate. The solvent was distilled off under reduced pressure. The residues were purified by silica gel column chromatography (n-hexane/ethyl acetate=4/1) to obtain 0.15 g of the intended product (92% ee). (yield: 88%)

The optical purity was calculated from the percentage of the area of the chromatogram of HPLC (solvent: n-hexane/isopropanol=80/1, UV=210) equipped with an optically active column ("Chiralcell OJ").

EXAMPLE 7-2

Production of (S)-1-(2,4-dichlorophenyl)-2-chloro-1-ethanol 126.7 g of (S)-2-chloro-1-(2,4-dichlorophenyl)ethylhydrogenphthalate (0.339 mol) were dissolved in 600 ml of n-propanol. The solution was added with 34.4 g of triethylamine (0.339 mol) and reacted under reflux for 4 hours. After the reaction was completed, the solution was cooled to the room temperature and the solvent was distilled off under reduced pressure. The intended product was extracted with 500 ml of ethyl acetate. The ethyl acetate layer was washed with 100 ml of 1N-HCl, 200 ml of brine, 200 ml of 10% sodium carbonate aqueous solution and 200 ml of brine, in that order. After the ethyl acetate layer was dried over anhydrous magnesium sulfate, the solvent was distilled off under reduced pressure to obtain 74.5 g of (s)-1-(2,4-dichlorophenyl)-2-chloro-1-ethanol. (optical purity: 95% ee, yield 97.4%)

EXAMPLE 8

Racemization of the optically active 2-chloro-1-(2, 4-dichlorophenyl)ethanol

The filtrate obtained at the time of the optical resolution of diastereomer salts in Example 4 was concentrated and subjected to double decomposition in the same manner as in Example 4. The resulting (R)-(2-chloro-1-(2,4-dichlorophenyl)ethyl) hydrogenphthalate was hydrolyzed in the same manner in Example 5 to obtain 0.25 g of (R)-1-(2,4-dichlorophenyl)-2-chloro- 1-ethanol (48% ee). The obtained product (0.2 g) was dissolved in a mixture of 8 ml of trifluoroacetic acid and 2 ml of water. The solution was refluxed for 8 hours. After the reaction was completed, the solvent was distilled off under reduced pressure to obtain 0.19 g of the intended product (0% ee). (yield: 93%)

The optical purity was calculated from the percentage of the area of the chromatogram of HPLC (solvent: n-hexane/isopropanol=80/1, UV=210) equipped with an optically active column ("Chiralcel OJ").

EXAMPLE 9

Racemization of the optically active 2-chloro-1-(2, 4-dichlorophenyl)ethanol 0.2 g of (R)-2-chloro-1-(2,4-dichlorophenyl)ethanol (48% ee) which was obtained in the similar method to Example 8, was dissolved in a mixed solvent composed of 120 ml of 18N-sulfuric acid and 90 ml of 1,2-dimethoxyethane. The solution was refluxed for 3 hours. After the reaction was completed, the solvent was concentrated under reduced pressure. The residues were poured into water and the aqueous solution was neutralized with sodium hydrogen carbonate. The intended product was extracted with ethyl acetate from the aqueous layer. The organic layer was washed with water and dried with anhydrous magnesium sulfate, and the solvent was distilled off under reduced pressure to obtain 1.0 g of the intended product (0% ee). (yield: 83%)

The optical purity was calculated from the percentage of the area of the chromatogram of HPLC (solvent: n-hexane/isopropanol=80/1, UV=230) equipped with an optically active column ("Chiralcel OJ").

Optically active 2-chloro-1-(2,4-dichlorophenyl)ethanol may be converted into its hydrogenphthalate by the same manner with the Example 2 and be purified by recrystallization method to heighten its optical purity.

The lowering of optical purity by phthalization can be negligible. For example, when 80% ee of 2-chloro-1-(2,4-dichlorophenyl)ethanol is used, optical purity of phthalate is 76.7% ee.

The following is examples conducted in accordance with recrystallization.

EXAMPLE 10-1

4.6 g of (S)-(2-chloro-1-(2,4-dichlorophenyl)ethyl) hydrogenphthalate (optical purity: 95.7%) was heated and dissolved in 60 ml of chloroform. After the addition of 60 ml of n-hexane, the solution was scratched under ice-cooling to be crystallized and left at 0° C. for 5 hours to precipitate (S)-2-chloro-1-(2,4-dichlorophenyl)ethyl hydrogenphthalate. (optical purity: 99% ee, yield: 93.5%)

Table 3 shows a result that (S)-2-chloro-1-(2,4-dichlorophenyl)ethyl hydrogenphthalate having various degree of optical purity are used and examined.

TABLE 3

| Example No. | Optical purity before production (% ee) | Optical purity after production (% ee) |
|---|---|---|
| 10-2 | 69.4 | 84. 6 |
| 10-3 | 89.0 | 96.8 |

Referential Example 1

Production of (S)-2-chloro-1-(2,4-dichlorophenyl) ethanol as the reference substance for analysis To 5 ml of dry tetrahydrofuran were dropwise added 0.3 g of (S)-3,3-diphenyl-1-methyltetrahydro-1H,3H-pyrrolo-[1,2,-C]-[1,3,2] oxazaborol and 8 ml of 1.0M solution of borane in THF at −20° C . 5 ml of dried THF solution containing 2.2 g of 2,4-dichlorophenacyl chloride was added dropwise at the same temperature. After warming to room temperature, 2 ml of methanol was added to decompose unreacted borane, and the reaction mixture was poured into water. The desired product was extracted with diethyl ether. The organic layer was washed with water and dried with anhydrous magnesium sulfate. The solvent was distilled off under reduced pressure. The residues were purified by silica gel column chromatography (ethyl acetate/n-hexane=1/5) to obtain 2.0 g of the intended product (80% ee). (yield: 92%)

What is claimed is:

1. A process for producing 2-halo-1-(substituted phenyl) ethanol of a formula (II):

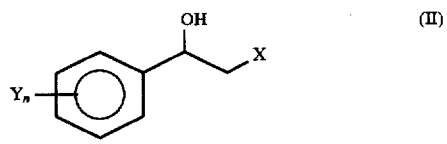

wherein X represents a halogen atom, Y is same or different and represents a hydrogen atom, a halogen atom, a $C_1$–$C_6$ alkyl group, a $C_1$–$C_6$ alkoxy group, a $C_1$–$C_6$ haloalkyl group or a $C_1$–$C_6$ haloalkoxy group and n is 0 or an integer of 1 to 3, comprising racemizing a compound of a formula (Ia):

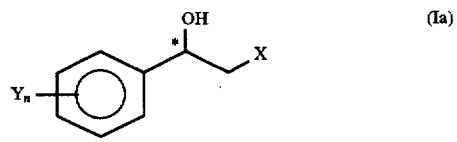

wherein X, Y and n have the same meaning as defined above and * represents an asymmetric carbon atom, with an acid.

2. A process for producing a racemic compound (II) as described in claim 1, wherein X represents a halogen atom, Y represent a hydrogen atom, a halogen atom, a $C_1$–$C_6$ alkyl group or a $C_1$–$C_6$ alkoxy group, and n is an integer of 1 to 2.

3. A process for producing a racemic compound (II) as described in claim 1, wherein X represents a chlorine atom, Y represent a hydrogen atom, a $C_1$–$C_6$ alkyl group or a $C_1$–$C_2$ alkoxy group, and n is an integer of 1 to 2.

* * * * *